United States Patent
Peel et al.

(10) Patent No.: US 12,203,081 B2
(45) Date of Patent: Jan. 21, 2025

(54) CANNABIS UBIQUITIN PROMOTER

(71) Applicant: Phylos Bioscience, Inc., Portland, OR (US)

(72) Inventors: Gregory Peel, Portland, OR (US); Kayla Hardwick, Portland, OR (US); Jessica Staha, Portland, OR (US); Alisha Holloway, Portland, OR (US)

(73) Assignee: Phylos Bioscience, Inc., Portland, OR (US)

( * ) Notice: Subject to any disclaimer, the term of this patent is extended or adjusted under 35 U.S.C. 154(b) by 0 days.

(21) Appl. No.: 17/766,528

(22) PCT Filed: Oct. 9, 2020

(86) PCT No.: PCT/US2020/054911
§ 371 (c)(1),
(2) Date: Apr. 4, 2022

(87) PCT Pub. No.: WO2021/086576
PCT Pub. Date: May 6, 2021

(65) Prior Publication Data
US 2024/0084317 A1    Mar. 14, 2024

Related U.S. Application Data

(60) Provisional application No. 62/928,753, filed on Oct. 31, 2019.

(51) Int. Cl.
*C12N 15/82* (2006.01)
*C07K 14/415* (2006.01)

(52) U.S. Cl.
CPC ........ *C12N 15/8216* (2013.01); *C07K 14/415* (2013.01)

(58) Field of Classification Search
None
See application file for complete search history.

(56) References Cited

U.S. PATENT DOCUMENTS

| | | |
|---|---|---|
| 5,510,474 A | 4/1996 | Quail et al. |
| 2021/0180077 A1 | 6/2021 | Gordon-Kamm et al. |

FOREIGN PATENT DOCUMENTS

| | | |
|---|---|---|
| WO | WO 2001/094394 A2 | 12/2001 |
| WO | WO 2022/046957 A2 | 3/2022 |

OTHER PUBLICATIONS

Gloss, An overview of products and bias in research, 2015, Neurotherapeutics, vol. 12, pp. 731-734. (Year: 2015).*
Kawazu et al., Lettuce polyubiquitin promoter-terminator promotes transgene expression transcriptionally in lettuce and translationally in both lettuce and *Arabidopsis*, 2019, The Horticulture Journal, vol. 88(1), pp. 83-91. (Year: 2019).*
Predicted: Cannabis sativa polyubiquitin (LOC115702720), mRNA, NCBI Reference Sequence: XM_030630147.1, 2019 (Year: 2019).*
Deikman et al., Organization of Ripening and Ethylene Regulatory Regions in a Fruit-Specific Promoter from Tomato (*Lycopersicon esculentum*), 1992, Plant Physiology, vol. 100, pp. 2013-2017. (Year: 1992).*
Doelling et al., The minimal ribosomal RNA gene promoter of *Arabidopsis thaliana* includes a critical element at the transcription initiation site, 1995, The Plant Journal, vol. 8(5), pp. 683-692. (Year: 1995).*
Predicted: Lactuca sativa polyubiquitin-like (LOC111905137), mRNA NCBI Reference Sequence: XM_023900808.1, 2018. (Year: 2018).*
Feeney et al., Tissue culture and Agrobacterium-mediated transformation of hemp (*Cannabis sativa* L.), 2003, In Vitro Cellular & Developmental Biology—Plant, vol. 39, pp. 578-585. (Year: 2003).*
Authors: Takaki Maekawa, Mitsumasa Kusakabe, Yoshikazu Shimoda, Shusei Sato, Satoshi Tabata, Yoshikatsu Murooka, and Makoto Hayashi; Title: Polyubiquitin Promoter-Based Binary Vectors for Overexpression and Gene Silencing in Lotus japonicus; Publishing Information: MPMI vol. 21, No. 4, 2008, pp. 375-382. doi:10.1094/MPMI -21-4-0375. © 2008 The American Phytopathological Society, Japan.
Author: Federal Institute of Industrial Property; Title: International Search Report regarding Applicant's file reference 2001-WOI / International Application No. PCT/US 2020/054911; Date of Completion: Dec. 8, 2020, Moscow, Russia.
Author: Federal Institute of Industrial Property; Title: Written Opinion of the International Searching Authority regarding 2001-WO1 / International Application No. PCT/US 2020/054911; Date of Completion: Dec. 8, 2020, Moscow, Russia.
Kawazu Y. et al. Lettuce Polyubiquitin Promoter-terminator Promotes Transgene Expression Transcriptionally in Lettuce and Translationally in both Lettuce and *Arabidopsis*. The Horticulture Journal, 2019, vol. 88, Issue 1, pp. 83-91, Released Jan. 31, 2019, abstract.
Predicted: Cannabis sativa polyubiquitin (LOC115702720), mRNA. Database NCBI Reference Sequence: XM_030630147.1, Aug. 28, 2019.

* cited by examiner

*Primary Examiner* — Amjad Abraham
*Assistant Examiner* — Christina L Meadows
(74) *Attorney, Agent, or Firm* — Klarquist Sparkman, LLP

(57) ABSTRACT

Provided herein is the identification and use of the Cannabis Ubiquitin promoter and its use in promoting the expression of one or more heterologous nucleic acid fragments in a constitutive manner in Cannabis plants. The invention further discloses compositions, polynucleotide constructs, transformed host cells, plants and seeds containing the recombinant construct with the promoter, and methods for preparing and using the same.

20 Claims, 5 Drawing Sheets
Specification includes a Sequence Listing.

CANNABIS UBIQUITIN PROMOTER

This application is a national stage application of PCT Application No. PCT/US2020/54911, filed Oct. 9, 2020, which claims priority benefit to U.S. Provisional Application No. 62/928,753, filed Oct. 31, 2019, the entire contents of which are hereby incorporated by reference.

SEQUENCE LISTING REFERENCE

Pursuant to 37 CFR §§ 1.821-1.825, a Sequence Listing in the form of an ASCII-compliant text file (entitled "Sequence_Listing_2001-US1_ST25.txt" created on Sep. 2, 2020, and 11,150 bytes in size), which will serve as both the paper copy required by 37 CFR § 1.821(c) and the computer readable form (CRF) required by 37 CFR § 1.821(e), is submitted concurrently with the instant application. The entire contents of the Sequence Listing are incorporated herein by reference.

BACKGROUND OF THE INVENTION

In eukaryotic systems expression of genes is directed by a region of the DNA sequence called a promoter. The promoter is considered to be that portion of the DNA, upstream from the coding region, which contains the binding site for RNA polymerase II and initiates transcription of the DNA. The promoter region also comprises other elements that act as regulators of gene expression. These include a TATA box consensus sequence in the vicinity of about −30, and often a CAAT box consensus sequence at about −75 bp 5' relative to the transcription start site, or cap site, which is defined as +1 (R. Breathnach and P. Chambon (1981) Ann. Rev. Biochem. 50:349-383; J. Messing et al. (1983) in Genetic Engineering of Plants, eds. T. Kosuge, C. P. Meredith and A. Hollaender, pp. 211-227). In plants the CAAT box may be substituted by the AGGA box (J. Messing et al. (1983) supra). RNA polymerase binding aligns the RNA polymerase so that transcription will initiate at a specific transcription initiation site. Furthermore, the nucleotide sequence of the promoter determines the nature of the RNA polymerase binding and other related protein factors that attach to the RNA polymerase and/or promoter, and the rate of RNA synthesis. The RNA is then processed to produce messenger RNA (mRNA) which serves as a template for translation of the RNA sequence into the amino acid sequence of the encoded polypeptide. Constitutive promoters direct RNA synthesis at relatively equal levels across all tissues of a plant, which is useful to drive heterologous expression.

A well known constitutive promoter is the ubiquitin promoter. Ubiquitin is an 8.5 kDa protein found in eukaryotic cells in either the free, monomeric state or covalently joined to various cytoplasmic, nuclear or membrane proteins. This protein contains 76 amino acid residues and its amino acid sequence is conserved to an unusually high extent. The sequence of ubiquitin is identical between species as diverse as human, cow, Mediterranean fruit fly, Xenopus and chicken (U. Bond and M. Schlesinger (1985) Mol. Cell. Biol. 5:949-956). Yeast and human ubiquitin differ by only three different amino acids (K. Ozkaynak et al. (1984) Nature 312:663-666), while plant ubiquitin differs from that of yeast by two amino acids. Based on this two or three amino acid difference in sequence, there appear to be at least 3 types of ubiquitin—animal, plant and yeast. The invention described herein identifies the Cannabis Ubiquitin protomer and its use in driving constitutive heterologous expression in Cannabis plants.

SUMMARY OF THE INVENTION

The present teachings relate to heterologous nucleotide and protein expression in Cannabis. In one embodiment, a recombinant DNA construct is provided. The construct comprises a polynucleotide sequence having at least 90% sequence identity to SEQ ID NO:3. In an embodiment, the polynucleotide sequence is operably linked to at least one heterologous polynucleotide sequence to be expressed. In an embodiment, the construct further comprises a polynucleotide sequence with a selectable marker. In an embodiment, the construct further comprises a 3' untranslated polynucleotide sequence. In an embodiment, the construct further comprises a 5' untranslated polynucleotide sequence. In an embodiment, the construct further comprises one or more intron polynucleotide sequences. In an embodiment, the heterologous polynucleotide sequence is a Cannabis polynucleotide sequence. In an embodiment, the at least one heterologous polynucleotide sequence comprises a polynucleotide sequence selected from the group consisting of: a reporter nucleotide sequence, a selection marker nucleotide sequence, a nucleotide sequence conferring disease resistance, a nucleotide sequence conferring herbicide resistance, a nucleotide sequence conferring insect resistance, a gene-editing nucleotide sequence, a nucleotide sequence involved in carbohydrate metabolism, a nucleotide sequence involved in fatty acid metabolism, a nucleotide sequence invoked in amino acid metabolism, a nucleotide sequence involved in plant or tissue development, a nucleotide sequence involved in plant growth regulation, a nucleotide sequence involved in yield improvement, a nucleotide sequence involved in drought resistance, a nucleotide sequence involved in cold resistance, a nucleotide sequence involved in heat resistance, and a nucleotide sequence involved in salt resistance in plants. In an embodiment, the at least one heterologous polynucleotide sequence encodes a protein selected from the group consisting of: a reporter protein, a selection marker, a protein conferring disease resistance, a protein conferring herbicide resistance, a protein conferring insect resistance, a gene editing protein, a protein involved in carbohydrate metabolism, a protein involved in fatty acid metabolism, a protein involved in amino acid metabolism, a protein involved in plant or tissue development, a protein involved in plant growth regulation, a protein involved in yield improvement, a protein involved in drought resistance, a protein involved in cold resistance, a protein involved in heat resistance, and a protein involved in salt resistance in plants.

In another embodiment a cell comprising a recombinant DNA construct is provided wherein the construct comprises a polynucleotide sequence having at least 90% sequence identity to SEQ ID NO:3. In an embodiment, the polynucleotide sequence is operably linked to at least one heterologous polynucleotide sequence to be expressed. In an embodiment, the construct further comprises a polynucleotide sequence with a selectable marker. In an embodiment, the construct further comprises a 3' untranslated polynucleotide sequence. In an embodiment, the construct further comprises a 5' untranslated polynucleotide sequence. In an embodiment, the construct further comprises one or more intron polynucleotide sequences. In an embodiment, the heterologous nucleotide sequence is a Cannabis polynucleotide sequence. In an embodiment, the at least one heterologous polynucleotide sequence comprises a polynucleotide sequence selected from the group consisting of: a reporter nucleotide sequence, a selection marker nucleotide sequence, a nucleotide sequence conferring disease resistance, a nucleotide sequence conferring herbicide resistance, a nucleotide sequence conferring insect resistance, a gene-editing nucleotide sequence, a nucleotide sequence involved in carbohydrate metabolism, a nucleotide sequence involved in fatty acid metabolism, a nucleotide sequence invoked in amino acid metabolism, a nucleotide sequence involved in plant or tissue development, a nucleotide sequence involved in plant growth regulation, a nucleotide sequence involved in yield improvement, a nucleotide sequence involved in drought resistance, a nucleotide sequence involved in cold resistance, a nucleotide sequence involved in heat resistance, and a nucleotide sequence involved in salt resistance in plants. In an embodiment, the at least one heterologous polynucleotide sequence encodes a protein selected from the group consisting of: a reporter protein, a selection marker, a protein conferring disease resistance, a protein conferring herbicide resistance, a protein conferring insect resistance, a gene editing protein, a protein involved in carbohydrate metabolism, a protein involved in fatty acid metabolism, a protein involved in amino acid metabolism, a protein involved in plant or tissue development, a protein involved in plant growth regulation, a protein involved in yield improvement, a protein involved in drought resistance, a protein involved in cold resistance, a protein involved in heat resistance, and a protein involved in salt resistance in plants. In an embodiment, the cell is a plant cell. In an embodiment, the plant cell is a Cannabis plant cell.

In another embodiment, a transgenic plant comprising a recombinant DNA construct is provided wherein the construct comprises a polynucleotide sequence having at least 90% sequence identity to SEQ ID NO:3. In an embodiment, the polynucleotide sequence is operably linked to at least one heterologous polynucleotide sequence to be expressed. In an embodiment, the construct further comprises a polynucleotide sequence with a selectable marker. In an embodiment, the construct further comprises a 3' untranslated polynucleotide sequence. In an embodiment, the construct further comprises a 5' untranslated polynucleotide sequence. In an embodiment, the construct further comprises one or more intron polynucleotide sequences. In an embodiment, the heterologous polynucleotide sequence is a cannabis polynucleotide sequence. In an embodiment, the at least one heterologous polynucleotide sequence comprises a polynucleotide sequence selected from the group consisting of: a reporter nucleotide sequence, a selection marker nucleotide sequence, a nucleotide sequence conferring disease resistance, a nucleotide sequence conferring herbicide resistance, a nucleotide sequence conferring insect resistance, a gene-editing nucleotide sequence, a nucleotide sequence involved in carbohydrate metabolism, a nucleotide sequence involved in fatty acid metabolism, a nucleotide sequence invoked in amino acid metabolism, a nucleotide sequence involved in plant or tissue development, a nucleotide sequence involved in plant growth regulation, a nucleotide sequence involved in yield improvement, a nucleotide sequence involved in drought resistance, a nucleotide sequence involved in cold resistance, a nucleotide sequence involved in heat resistance, and a nucleotide sequence involved in salt resistance in plants. In an embodiment, the at least one heterologous polynucleotide sequence encodes a protein selected from the group consisting of: a reporter protein, a selection marker, a protein conferring disease resistance, a protein conferring herbicide resistance, a protein conferring insect resistance, a gene editing protein, a protein involved in carbohydrate metabolism, a protein involved in fatty acid metabolism, a protein involved in amino acid metabolism, a protein involved in plant or tissue development, a protein involved in plant growth regulation, a protein involved in yield improvement, a protein involved in drought resistance, a protein involved in cold resistance, a protein involved in heat resistance, and a protein involved in salt resistance in plants. In an embodiment, the plant is a Cannabis plant. In an embodiment, the heterologous protein is expressed in one or more trichomes of the Cannabis plant. In an embodiment, the recombinant DNA construct is stably incorporated into the plant's genome.

In another embodiment, a method for altering the expression of at least one heterologous nucleic acid fragment in a plant is provided. The method comprises (a) transforming a cell of the plant with a recombinant DNA construct comprising a polynucleotide sequence having at least 90% sequence identity to SEQ ID NO:3, (b) growing fertile mature plants from the transformed plant cell of step (a); and (c) selecting plants containing the transformed plant cell wherein the expression of the heterologous nucleic acid fragment is increased in the number of cells of the plant. In an embodiment, the polynucleotide sequence is operably linked to at least one heterologous polynucleotide sequence to be expressed. In an embodiment, the construct further comprises a polynucleotide sequence with a selectable marker. In an embodiment, the construct further comprises a 3' untranslated polynucleotide sequence. In an embodiment, the construct further comprises a 5' untranslated polynucleotide sequence. In an embodiment, the construct further comprises one or more intron polynucleotide sequences. In an embodiment, the heterologous polynucleotide sequence is a cannabis nucleotide sequence. In an embodiment, the at least one heterologous polynucleotide sequence comprises a polynucleotide sequence selected from the group consisting of: a reporter nucleotide sequence, a selection marker nucleotide sequence, a nucleotide sequence conferring disease resistance, a nucleotide sequence conferring herbicide resistance, a nucleotide sequence conferring insect resistance, a gene-editing nucleotide sequence, a nucleotide sequence involved in carbohydrate metabolism, a nucleotide sequence involved in fatty acid metabolism, a nucleotide sequence invoked in amino acid metabolism, a nucleotide sequence involved in plant or tissue development, a nucleotide sequence involved in plant growth regulation, a nucleotide sequence involved in yield improvement, a nucleotide sequence involved in drought resistance, a nucleotide sequence involved in cold resistance, a nucleotide sequence involved in heat resistance, and a nucleotide sequence involved in salt resistance in plants. In an embodiment, the at least one heterologous polynucleotide sequence encodes a protein selected from the group consisting of: a reporter protein, a selection marker, a protein conferring disease resistance, a protein conferring herbicide resistance, a protein conferring insect resistance, a gene editing protein, a protein involved in carbohydrate metabolism, a protein involved in fatty acid metabolism, a protein involved in amino acid metabolism, a protein involved in plant or tissue development, a protein involved in plant growth regulation, a protein involved in yield improvement, a protein involved in drought resistance, a protein involved in cold resistance, a protein involved in heat resistance, and a protein involved in salt resistance in plants. In an embodiment, the plant is a Cannabis plant. In an embodiment, the heterologous protein is expressed in one or more trichomes of the Cannabis plant. In an embodiment, the recombinant DNA construct is stably incorporated into the plant's genome.

BRIEF DESCRIPTION OF THE DRAWINGS

The skilled artisan will understand that the drawings, described below, are for illustration purposes only. The drawings are not intended to limit the scope of the present teachings in any way.

FIG. 4 illustrates the proof of concept using a Cannabis promoter dsRED reporter construct (CsUBQ-DsRED) driving dsRED expression in lettuce.

DETAILED DESCRIPTION OF THE INVENTION

Figure 1:
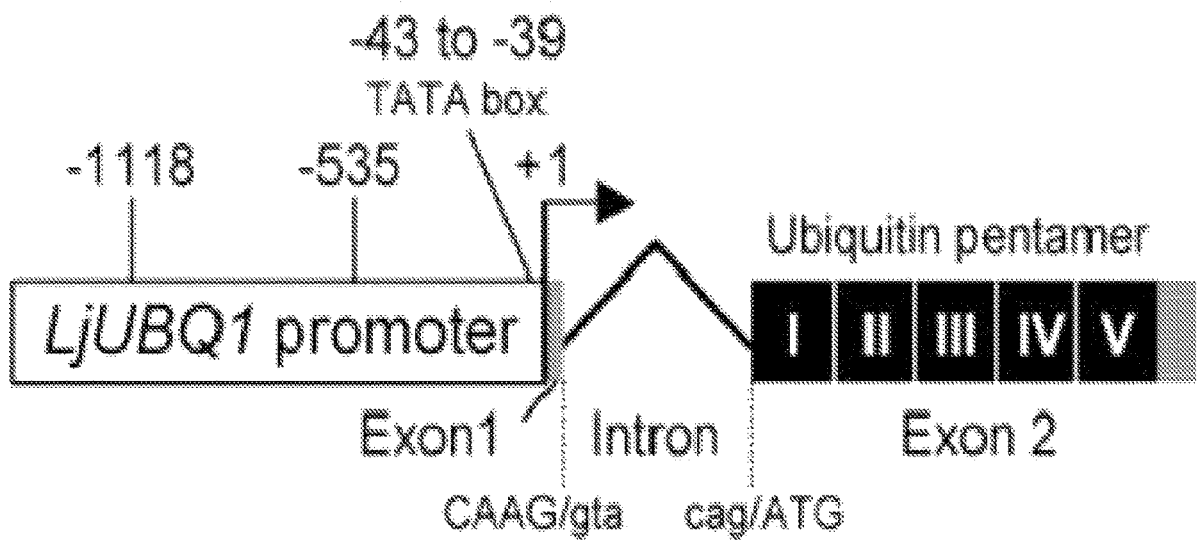
FIG. 1 illustrates the ubiquitin gene structure from Lotus.

These and other features of the present teachings will become more apparent from the description herein. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The present teachings relate generally to Cannabis Ubiquitin promoters and their use in driving heterologous expression in Cannabis plants.

The terminology used in the disclosure herein is for the purpose of describing particular embodiments only and is not intended to be limiting of the disclosure. As used in the description of the embodiments of the disclosure and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, amount, dose, time, temperature, for example, is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this disclosure belongs.

Definitions

The phrase "altering expression" refers to the production of gene product(s) in transgenic organisms in amounts or proportions that differ significantly from the amount of the gene product(s) produced by the corresponding wild-type organisms (i.e., expression is increased or decreased).

The term "Cannabis" refers to plants of the genus Cannabis, *including Cannabis sativa, Cannabis indica,* and *Cannabis ruderalis.*

The term "cell" refers to a prokaryotic or eukaryotic cell, including plants cells, capable of replicating DNA, transcribing RNA, translating polypeptides, and secreting proteins.

The term "coding sequence" refers to a DNA sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

The term "codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

The term "constitutive promoter" refers to promoters active in all or most tissues or cell types of a plant at all or most developing stages. As with other promoters classified as "constitutive" (e.g. ubiquitin), some variation in absolute levels of expression can exist among different tissues or stages. The term "constitutive promoter" or "tissue-independent" are used interchangeably herein.

The terms "construct," "plasmid," "vector," and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. The term "recombinant DNA construct" or "recombinant expression construct" is used interchangeably and refers to a discrete polynucleotide into which a nucleic acid sequence or fragment can be moved. Preferably, it is a plasmid vector or a fragment thereof comprising the promoters of the present invention. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

The term "expression" or "gene expression" relates to the process by which the coded information of a nucleic acid transcriptional unit (including, e.g., genomic DNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

The term "expression cassette" refers to a discrete nucleic acid fragment into which a nucleic acid sequence or fragment can be moved.

The term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "genome" as it applies to plant cells encompasses not only chromosomal DNA found within the nucleus, but organelle DNA found within subcellular components (e.g., mitochondrial, plastid) of the cell.

The phrase "heterologous nucleotide sequence" refers to a sequence that is not naturally occurring with the plant promoter sequence of the invention. While this nucleotide sequence is heterologous to the promoter sequence, it may be homologous, or native, or heterologous, or foreign, to the plant host. However, it is recognized that the instant promoters may be used with their native coding sequences to increase or decrease expression resulting in a change in phenotype in the transformed seed. The terms "heterologous nucleotide sequence", "heterologous sequence", "heterologous nucleic acid fragment", and "heterologous nucleic acid sequence" are used interchangeably herein.

The terms "initiate transcription," "initiate expression," "drive transcription," and "drive expression" are used interchangeably herein and all refer to the primary function of a promoter. As detailed throughout this disclosure, a promoter is a non-coding genomic DNA sequence, usually upstream (5') to the relevant coding sequence, and its primary function is to act as a binding site for RNA polymerase and initiate transcription by the RNA polymerase. Additionally, there is "expression" of RNA, including functional RNA, or the expression of polypeptide for operably linked encoding nucleotide sequences, as the transcribed RNA ultimately is translated into the corresponding polypeptide.

The term "introduced" refers to a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

The term "intron" refers to an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

The term "isolated" as used herein means having been removed from its natural environment, or removed from other compounds present when the compound is first formed. The term "isolated" embraces materials isolated from natural sources as well as materials (e.g., nucleic acids and proteins) recovered after preparation by recombinant expression in a host cell, or chemically-synthesized compounds such as nucleic acid molecules, proteins, and peptides.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The terms "percent sequence identity" or "percent identity" or "identity" are used interchangeably to refer to a sequence comparison based on identical matches between correspondingly identical positions in the sequences being compared between two or more amino acid or nucleotide sequences. The percent identity refers to the extent to which two optimally aligned polynucleotide or peptide sequences are invariant throughout a window of alignment of components, e.g., nucleotides or amino acids. Hybridization experiments and mathematical algorithms known in the art may be used to determine percent identity. Many mathematical algorithms exist as sequence alignment computer programs known in the art that calculate percent identity. These programs may be categorized as either global sequence alignment programs or local sequence alignment programs.

The term "plant" refers to whole plant and any descendant, cell, tissue, or part of a plant. A class of plant that can be used in the present invention is generally as broad as the class of higher and lower plants amenable to mutagenesis including angiosperms (monocotyledonous and dicotyledonous plants), gymnosperms, ferns and multicellular algae. Thus, "plant" includes dicot and monocot plants. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks. Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root. A plant cell is the structural and physiological unit of the plant, comprising a protoplast and a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein. In an embodiment described herein are plants in the genus of Cannabis and plants derived thereof, which can be produced asexual or sexual reproduction.

The terms "polynucleotide," "polynucleotide sequence," "nucleotide," "nucleotide sequence," "nucleic acid sequence," "nucleic acid fragment," and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide. An "isolated polynucleotide" refers to a polymer of ribonucleotides (RNA) or deoxyribonucleotides (DNA) that is single- or double-stranded, optionally containing synthetic, non-natural or altered nucleotide bases. An isolated polynucleotide in the form of DNA may be comprised of one or more segments of cDNA, genomic DNA or synthetic DNA.

The term "promoter" refers to a nucleic acid fragment capable of controlling transcription of another nucleic acid fragment. A promoter is capable of controlling the expression of a coding sequence or functional RNA. Functional RNA includes, but is not limited to, transfer RNA (tRNA) and ribosomal RNA (rRNA). The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. New promoters of various types useful in plant cells are constantly being discovered; numerous examples may be found in the compilation by Okamuro and Goldberg (Biochemistry of Plants 15:1-82 (1989)). It is further recognized that since in most cases the exact boundaries of regulatory sequences have not been completely defined, DNA fragments of some variation may have identical promoter activity.

The term "purified" as used herein relates to the isolation of a molecule or compound in a form that is substantially free of contaminants normally associated with the molecule or compound in a native or natural environment, or substantially enriched in concentration relative to other compounds present when the compound is first formed, and means having been increased in purity as a result of being separated from other components of the original composition. The term "purified nucleic acid" is used herein to describe a nucleic acid sequence which has been separated, produced apart from, or purified away from other biological compounds including, but not limited to polypeptides, lipids and carbohydrates, while effecting a chemical or functional change in the component (e.g., a nucleic acid may be purified from a chromosome by removing protein contaminants and breaking chemical bonds connecting the nucleic acid to the remaining DNA in the chromosome).

The terms "PCR" or "Polymerase Chain Reaction" refers to a technique for the synthesis of large quantities of specific DNA segments, consisting of a series of repetitive cycles (Perkin Elmer Cetus Instruments®, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

The term "polyadenylation signal" designates a nucleic acid sequence present in mRNA transcripts that allows for transcripts, when in the presence of a poly-(A) polymerase, to be polyadenylated on the polyadenylation site, for example, located 10 to 30 bases downstream of the poly-(A) signal. Many polyadenylation signals are known in the art and are useful for the present invention. An exemplary sequence includes AAUAAA and variants thereof, as described in Loke J., et al., (2005) Plant Physiology 138(3); 1457-1468.

The term "progeny" refers to any subsequent generation of a plant.

The term "protein" refers to amino acid polymers that contain at least five constituent amino acids that are covalently joined by peptide bonds. The constituent amino acids can be from the group of amino acids that are encoded by the genetic code, which include: alanine, valine, leucine, isoleucine, methionine, phenylalanine, tyrosine, tryptophan, serine, threonine, asparagine, glutamine, cysteine, glycine, proline, arginine, histidine, lysine, aspartic acid, and glutamic acid. As used herein, the term "protein" is synonymous with the related terms "peptide" and "polypeptide".

The term "RNA transcript" refers to a product resulting from RNA polymerase-catalyzed transcription of a DNA sequence. When an RNA transcript is a perfect complementary copy of a DNA sequence, it is referred to as a primary transcript or it may be a RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded by using the Klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcripts accumulation of a target gene (U.S. Pat. No. 5,107,065). The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated but yet has an effect on cellular processes.

The terms "similar," "substantially similar" and "corresponding substantially" as used herein refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences. A "substantially homologous sequence" refers to variants of the disclosed sequences such as those that result from site-directed mutagenesis, as well as synthetically derived sequences. A substantially homologous sequence of the present invention also refers to those fragments of a particular promoter nucleotide sequence disclosed herein that operate to promote the constitutive expression of an operably linked heterologous nucleic acid fragment. These promoter fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989. Again, variants of these promoter fragments, such as those resulting from site-directed mutagenesis, are encompassed by the compositions of the present invention.

The term "selectable marker gene" as used herein defines a gene or other expression cassette which encodes a protein which facilitates identification of cells into which the selectable marker gene is inserted. For example a "selectable marker gene" encompasses reporter genes as well as genes used in plant transformation to, for example, protect plant cells from a selective agent or provide resistance/tolerance to a selective agent. In one embodiment only those cells or plants that receive a functional selectable marker are capable of dividing or growing under conditions having a selective agent. Examples of selective agents can include, for example, antibiotics, including spectinomycin, neomycin, kanamycin, paromomycin, gentamicin, and hygromycin. These selectable markers include neomycin phosphotransferase (npt II), which expresses an enzyme conferring resistance to the antibiotic kanamycin, and genes for the related antibiotics neomycin, paromomycin, gentamicin, and G418, or the gene for hygromycin phosphotransferase (hpt), which expresses an enzyme conferring resistance to hygromycin. Other selectable marker genes can include genes encoding herbicide resistance including bar or pat (resistance against glufosinate ammonium or phosphinothricin), acetolactate synthase (ALS, resistance against inhibitors such as sulfonylureas (SUs), imidazolinones (IMIs), triazolopyrimidines (TPs), pyrimidinyl oxybenzoates (POBs), and sulfonylamino carbonyl triazolinones that prevent the first step in the synthesis of the branched-chain amino acids), glyphosate, 2,4-D, and metal resistance or sensitivity. Examples of "reporter genes" that can be used as a selectable marker gene include the visual observation of expressed reporter gene proteins such as proteins encoding .beta.-glucuronidase (GUS), luciferase, green fluorescent protein (GFP), yellow fluorescent protein (YFP), DsRed, .beta.-galactosidase, chloramphenicol acetyltransferase (CAT), alkaline phosphatase, and the like. The phrase "marker-positive" refers to plants that have been transformed to include a selectable marker gene.

The terms "terminator" or "transcription terminator" is defined as the transcribed segment in the 3' terminus of pre-mRNAs or mature mRNAs. For example, longer stretches of DNA beyond "polyadenylation signal" site is transcribed as a pre-mRNA. This DNA sequence usually contains transcription termination signal for the proper processing of the pre-mRNA into mature mRNA.

The term "transformation" refers to both stable transformation and transient transformation. "Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms. "Transient transformation" refers to the introduction of a nucleic acid fragment into the nucleus, or DNA-containing organelle, of a host organism resulting in gene expression without genetically stable inheritance.

The term "transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation. The term "transgenic plant" refers to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

The term "transient expression" refers to the temporary expression of often reporter genes such as beta-glucuronidase (GUS), fluorescent protein genes ZS-GREEN1, ZS-YELLOW1 N1, AM-CYAN1, DS-RED in selected certain cell types of the host organism in which the transgenic gene is introduced temporally by a transformation method. The transformed materials of the host organism are subsequently discarded after the transient gene expression assay.

The term "translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., Molecular Biotechnology 3:225 (1995)).

The term "trichome" encompasses herein different types of trichomes, both glandular trichomes and/or non-glandular trichomes. "Trichome cells" refers to the cells making up the trichome structure, such as the gland, or secretory cells, base cells and stalk, or stripe cells, extra-cellular cavity and cuticle cells. Trichomes can also consist of one single cell.

The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

The terms "5' untranslated region" or "5' UTR" is defined as the untranslated segment in the 5' terminus of pre-mRNAs or mature mRNAs. For example, on mature mRNAs, a 5' UTR typically harbors on its 5' end a 7-methylguanosine cap and is involved in many processes such as splicing, polyadenylation, mRNA export towards the cytoplasm, identification of the 5' end of the mRNA by the translational machinery, and protection of the mRNAs against degradation.

As used herein, the term "3' untranslated region" or "3' UTR" is defined as the untranslated segment in a 3' terminus of the pre-mRNAs or mature mRNAs. For example, on mature mRNAs this region harbors the poly-(A) tail and is known to have many roles in mRNA stability, translation initiation, and mRNA export. In addition, the 3' UTR is considered to include the polyadenylation signal and transcription terminator.

Cannabis

Cannabis has long been used for drug and industrial purposes, fiber (hemp), for seed and seed oils, for medicinal purposes, and for recreational purposes. Industrial hemp products are made from Cannabis plants selected to produce an abundance of fiber. Some Cannabis strains have been bred to produce minimal levels of THC, the principal psychoactive constituent responsible for the psychoactivity associated with marijuana. Marijuana has historically consisted of the dried flowers of Cannabis plants selectively bred to produce high levels of THC and other psychoactive cannabinoids. Various extracts including hashish and hash oil are also produced from the plant.

Cannabis is an annual, dioecious, flowering herb. The leaves are palmately compound or digitate, with serrate leaflets. Cannabis normally has imperfect flowers, with staminate "male" and pistillate "female" flowers occurring on separate plants. It is not unusual, however, for individual plants to separately bear both male and female flowers (i.e., have monoecious plants). Although monoecious plants are often referred to as "hermaphrodites," true hermaphrodites (which are less common in Cannabis) bear staminate and pistillate structures on individual flowers, whereas monoecious plants bear male and female flowers at different locations on the same plant.

The life cycle of Cannabis varies with each variety but can be generally summarized into germination, vegetative growth, and reproductive stages. Because of heavy breeding and selection by humans, most Cannabis seeds have lost dormancy mechanisms and do not require any pre-treatments or winterization to induce germination (See Clarke, R C et al. "Cannabis: Evolution and Ethnobotany" University of California Press 2013). Seeds placed in viable growth conditions are expected to germinate in about 3 to 7 days. The first true leaves of a Cannabis plant contain a single leaflet, with subsequent leaves developing in opposite formation, with increasing number of leaflets. Leaflets can be narrow or broad depending on the morphology of the plant grown. Cannabis plants are normally allowed to grow vegetatively for the first 4 to 8 weeks. During this period, the plant responds to increasing light with faster and faster growth. Under ideal conditions, Cannabis plants can grow up to 2.5 inches a day, and are capable of reaching heights of up to 20 feet. Indoor growth pruning techniques tend to limit Cannabis size through careful pruning of apical or side shoots.

Cannabis is diploid, having a chromosome complement of 2n=20, although polyploid individuals have been artificially produced. The first genome sequence of Cannabis, which is estimated to be 820 Mb in size, was published in 2011 by a team of Canadian scientists (Bakel et al, "The draft genome and transcriptome of *Cannabis sativa*" Genome Biology 12:R102).

All known strains of Cannabis are wind-pollinated and the fruit is an achene. Most strains of Cannabis are short day plants, with the possible exception of *C. sativa* subsp. *sativa* var. *spontanea* (=*C. ruderalis*), which is commonly described as "auto-flowering" and may be day-neutral.

The genus Cannabis was formerly placed in the Nettle (Urticaceae) or Mulberry (Moraceae) family, and later, along with the Humulus genus (hops), in a separate family, the Hemp family (Cannabaceae sensu stricto). Recent phylogenetic studies based on cpDNA restriction site analysis and gene sequencing strongly suggest that the Cannabaceae sensu stricto arose from within the former Celtidaceae family, and that the two families should be merged to form a single monophyletic family, the Cannabaceae sensu lato.

Cannabis plants produce a unique family of terpenophenolic compounds called cannabinoids. Cannabinoids, terpenoids, and other compounds are secreted by glandular trichomes that occur most abundantly on the floral calyxes and bracts of female plants. As a drug it usually comes in the form of dried flower buds (marijuana), resin (hashish), or various extracts collectively known as hashish oil. There are at least 483 identifiable chemical constituents known to exist in the Cannabis plant (Rudolf Brennesien, 2007, Chemistry and Analysis of Phytocannabinoids (cannabinoids produced by Cannabis) and other Cannabis Constituents, In Marijuana and the Cannabinoids, ElSohly, ed.; incorporated herein by reference) and at least 85 different cannabinoids have been isolated from the plant (El-Alfy, Abir T, et al., 2010, "Antidepressant-like effect of delta-9-tetrahydrocannabinol and other cannabinoids isolated from *Cannabis sativa* L", Pharmacology Biochemistry and Behavior 95 (4): 434-42; incorporated herein by reference). The two cannabinoids usually produced in greatest abundance are cannabidiol (CBD) and/or $\Delta^9$-tetrahydrocannabinol (THC). THC is psychoactive while CBD is not. See, ElSohly, ed. (Marijuana and the Cannabinoids, Humana Press Inc., 321 papers, 2007), which is incorporated herein by reference in its entirety, for a detailed description and literature review on the cannabinoids found in marijuana.

Identification of a Novel Cannabis Ubiquitin Promoter

Ubiquitins are omnipresent proteins which have been found in all eukaryotes analyzed thus far. Thus, Kawalleck et al. (Plant Molecular Biology, 21, 1993: 673-684) describe two parsley (Petroselinum crispum) ubiquitins, ubi4-1 and ubi4-2. The promoter of ubi4-2 has been isolated. It was not possible to demonstrate any heat inducibility of ubi4-1 and ubi4-2 under the conditions studied by Kawalleck et al.

Ubiquitin is a polypeptide found in all eukaryotes and has been studied for its role in a wide range of cellular functions. Promoters of the ubiquitin gene have been isolated. For example, in U.S. Pat. Nos. 5,510,474, 5,614,399, 6,054,574 and 6,020,190 ubiquitin promoters are described which include a heat shock element and intron. Jilka, et al., describe another maize ubiquitin type promoter at U.S. Pat. No. 6,977,325. Xia, et al., identified a soybean genomic clone containing a ubiquitin gene (Xia, et al., (1994) Plant Physiol. 104:805-806). These sequences are reported at GenBank accession numbers D16248.1 and D2823.1. Also, Finer, et al., have discussed analysis of a soybean ubiquitin promoter, but did not provide a sequence (Finer, et al., (2006) "Characterization of soybean promoters through evaluation of GFP expression in transgenic soybean" The 11.sup.th Biennial Conference on the Molecular and Cellular Biology of the Soybean, Aug. 5-8, 2006, University of Nebraska, Lincoln, Nebr.).

The inventions described herein identifies a novel Cannabis Ubiquitin promoter and provides compositions and methods for heterologous gene expression driven by the Ubiquitin promoter. In one embodiment, a recombinant DNA construct comprising a Cannabis Ubiquitin promoter is provided, and in an embodiment the promoter is operably linked to at least one heterologous polynucleotide sequence to be expressed. In another embodiment a cell is provided comprising the recombinant DNA construct. In another embodiment a transgenic plant comprising the recombinant DNA construct is provided. In another embodiment, a method for altering expression of at least one heterologous nucleic acid fragment in a plant is provided comprising transforming a cell of the plant with the recombinant DNA construct.

Using BLAST algorithms as described herein are methods well known to those skilled in the art for identification of novel regulatory nucleotide sequences from analogous sequences in similar species.

Generating Promoter Constructs

Methods for construction of chimeric and variant promoters of the present invention include, but are not limited to, combining control elements of different promoters or duplicating portions or regions of a promoter (see for example, U.S. Pat. Nos. 4,990,607; 5,110,732; and 5,097,025). Those of skill in the art are familiar with the standard resource materials that describe specific conditions and procedures for the construction, manipulation, and isolation of macromolecules (e.g., polynucleotide molecules and plasmids), as well as the generation of recombinant organisms and the screening and isolation of polynucleotide molecules.

The isolated promoter sequence of the present invention can be modified to provide a range of constitutive expression levels of the heterologous nucleotide sequence. Thus, less than the entire promoter regions may be utilized and the ability to drive expression of the coding sequence retained. However, it is recognized that expression levels of the mRNA may be decreased with deletions of portions of the promoter sequences. Likewise, the tissue-independent, constitutive nature of expression may be changed.

Modifications of the isolated promoter sequences of the present invention can provide for a range of constitutive expression of the heterologous nucleotide sequence. Thus, they may be modified to be weak constitutive promoters or strong constitutive promoters. Generally, by "weak promoter" is intended a promoter that drives expression of a coding sequence at a low level. By "low level" is intended at levels about 1/10,000 transcripts to about 1/100,000 transcripts to about 1/500,000 transcripts. Conversely, a strong promoter drives expression of a coding sequence at high level, or at about 1/10 transcripts to about 1/100 transcripts to about 1/1,000 transcripts.

Moreover, the skilled artisan recognizes that substantially similar nucleic acid sequences encompassed by this invention are also defined by their ability to hybridize, under moderately stringent conditions (for example, 0.5×SSC, 0.1% SDS, 60 degrees celsius) with the sequences exemplified herein, or to any portion of the nucleotide sequences reported herein and which are functionally equivalent to the promoter of the invention. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U.K., 1985). Stringency conditions can be adjusted to screen for moderately similar fragments, such as homologous sequences from distantly related organisms, to highly similar fragments, such as genes that duplicate functional enzymes from closely related organisms.

In some aspects of the present invention, the promoter fragments can comprise at least about 20 contiguous nucleotides, or at least about 50 contiguous nucleotides, or at least about 75 contiguous nucleotides, or at least about 100 contiguous nucleotides, or at least about 150 contiguous nucleotides, or at least about 200 contiguous nucleotides, or at least about 250 contiguous nucleotides, or at least about 300 contiguous nucleotides, or at least about 350 contiguous nucleotides, or at least about 400 contiguous nucleotides, or at least about 450 contiguous nucleotides, or at least about 500 contiguous nucleotides, or at least about 550 contiguous nucleotides, or at least about 600 contiguous nucleotides, or at least about 650 contiguous nucleotides, or at least about 700 contiguous nucleotides, or at least about 750 contiguous nucleotides, or at least about 800 contiguous nucleotides, or at least about 850 contiguous nucleotides, or at least about 900 contiguous nucleotides, or at least about 950 contiguous nucleotides, or at least about 1000 of SEQ ID NO:3. The nucleotides of such fragments will usually comprise the TATA recognition sequence of the particular promoter sequence. Such fragments may be obtained by use of restriction enzymes to cleave the naturally occurring promoter nucleotide sequences disclosed herein, by synthesizing a nucleotide sequence from the naturally occurring promoter DNA sequence, or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989.

Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. It is well understood by one skilled in the art that many levels of sequence identity are useful in identifying related polynucleotide sequences. Useful examples of percent identities are those listed above, or also preferred is any integer percentage from 72% to 100%, such as 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%.

In an embodiment, an isolated polynucleotide is provided comprising a promoter wherein said promoter comprises a nucleotide sequence having at least 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity, based on the Clustal V method of alignment with pairwise alignment default parameters (KTUPLE=2, GAP PENALTY=5, WINDOW=4 and DIAGONALS SAVED=4) when compared to the nucleotide sequence of SEQ ID NO:3.

Local sequence alignment programs are similar in their calculation, but only compare aligned fragments of the sequences rather than utilizing an end-to-end analysis. Local sequence alignment programs such as BLAST can be used to compare specific regions of two sequences. A BLAST comparison of two sequences results in an E-value, or expectation value, that represents the number of different alignments with scores equivalent to or better than the raw alignment score, S, that are expected to occur in a database search by chance. The lower the E value, the more significant the match. Because database size is an element in E-value calculations, E-values obtained by BLASTing against public databases, such as GENBANK, have generally increased over time for any given query/entry match. In setting criteria for confidence of polypeptide function prediction, a "high" BLAST match is considered herein as having an E-value for the top BLAST hit of less than 1E-30; a medium BLASTX E-value is 1E-30 to 1E-8; and a low BLASTX E-value is greater than 1E-8. The protein function assignment in the present invention is determined using combinations of E-values, percent identity, query coverage and hit coverage. Query coverage refers to the percent of the query sequence that is represented in the BLAST alignment. Hit coverage refers to the percent of the database entry that is represented in the BLAST alignment. In one embodiment of the invention, function of a query polypeptide is inferred from function of a protein homolog where either (1) hit_p<1e-30 or % identity>35% AND query_coverage>50% AND hit_coverage>50%, or (2) hit_p<1e-8 AND query_coverage>70% AND hit_coverage>70%. The following abbreviations are produced during a BLAST analysis of a sequence. SEQ_NUM provides the SEQ ID NO for the listed recombinant polynucleotide sequences. CONTIG_ID provides an arbitrary sequence name taken from the name of the clone from which the cDNA sequence was obtained. PROTEIN_NUM provides the SEQ ID NO for the recombinant polypeptide sequence NCBI_GI provides the GenBank ID number for the top BLAST hit for the sequence. The top BLAST hit is indicated by the National Center for Biotechnology Information GenBank Identifier number. NCBI_GI_DESCRIPTION refers to the description of the GenBank top BLAST hit for sequence. E_VALUE provides the expectation value for the top BLAST match. MATCH_LENGTH provides the length of the sequence which is aligned in the top BLAST match TOP_HIT_PCT_IDENT refers to the percentage of identically matched nucleotides (or residues) that exist along the length of that portion of the sequences which is aligned in the top BLAST match. CAT_TYPE indicates the classification scheme used to classify the sequence. GO_BP=Gene Ontology Consortium—biological process; GO_CC=Gene Ontology Consortium—cellular component; GO_MF=Gene Ontology Consortium molecular function; KEGG=KEGG functional hierarchy (KEGG=Kyoto Encyclopedia of Genes and Genomes); EC=Enzyme Classification from ENZYME data bank release 25.0; POI=Pathways of Interest. CAT_DESC provides the classification scheme subcategory to which the query sequence was assigned. PRODUCT_CAT_DESC provides the FunCAT annotation category to which the query sequence was assigned. PRODUCT_HIT_DESC provides the description of the BLAST hit which resulted in assignment of the sequence to the function category provided in the cat_desc column. HIT_E provides the E value for the BLAST hit in the hit_desc column. PCT_IDENT refers to the percentage of identically matched nucleotides (or residues) that exist along the length of that portion of the sequences which is aligned in the BLAST match provided in hit_desc. QRY_RANGE lists the range of the query sequence aligned with the hit. HIT_RANGE lists the range of the hit sequence aligned with the query. provides the percent of query sequence length that matches QRY_CVRG provides the percent of query sequence length that matches to the hit (NCBI) sequence in the BLAST match (% qry cvrg=(match length/query total length)×100). HIT_CVRG provides the percent of hit sequence length that matches to the query sequence in the match generated using BLAST (% hit cvrg=(match lengthy hit total length)×100).

Methods for aligning sequences for comparison are well-known in the art. Various programs and alignment algorithms are described. In an embodiment, the subject disclosure relates to calculating percent identity between two polynucleotides or amino acid sequences using an AlignX alignment program of the Vector NTI suite (Invitrogen®, Carlsbad, Calif.). The AlignX alignment program is a global sequence alignment program for polynucleotides or proteins. In an embodiment, the subject disclosure relates to calculating percent identity between two polynucleotides or amino acid sequences using the MegAlign program of the LASERGENE® bioinformatics computing suite (MegAlign™ (.COPYRGT.1993-2016). DNASTAR. Madison, Wis.). The MegAlign program is global sequence alignment program for polynucleotides or proteins.

In some embodiments, the expression vectors of the present technology may contain termination sequences, which are positioned downstream of the nucleic acid molecules of the present technology, such that transcription of mRNA is terminated, and polyA sequences added. Exemplary terminators include Agrobacterium tumefaciens nopaline synthase terminator (Tnos), Agrobacterium tumefaciens mannopine synthase terminator (Tmas), and the CaMV 35S terminator (T35S). Termination regions include the pea ribulose bisphosphate carboxylase small subunit termination region (TrbcS) or the Tnos termination region. The expression vector also may contain enhancers, start codons, splicing signal sequences, and targeting sequences.

In some embodiments, the expression vectors of the present technology may contain a selection marker by which transformed cells can be identified in culture. The marker may be associated with the heterologous nucleic acid molecule, i.e., the gene operably linked to a promoter. In plants, for example, the marker gene will encode antibiotic or herbicide resistance. This allows for selection of transformed cells from among cells that are not transformed or transfected. Examples of suitable selectable markers include but are not limited to adenosine deaminase, dihydrofolate reductase, hygromycin-B-phosphotransferase, thymidine kinase, xanthine-guanine phospho-ribosyltransferase, glyphosate and glufosinate resistance, and amino-glycoside 3'-O-phosphotransferase (kanamycin, neomycin and G418 resistance). These markers may include resistance to G418, hygromycin, bleomycin, kanamycin, and gentamicin. The construct may also contain the selectable marker gene bar that confers resistance to herbicidal phosphinothricin analogs like ammonium gluphosinate. See, e.g., Thompson et al., EMBO J. 9:2519-23 (1987)). Other suitable selection markers known in the art may also be used. Visible markers such as green fluorescent protein (GFP) may be used. Methods for identifying or selecting transformed plants based on the control of cell division have also been described. See, e.g., WO 2000/052168 and WO 2001/059086.

One of ordinary skill in the art could perform the following non-limiting procedure based on the descriptions set forth herein: 1) operably link a nucleic acid fragment containing the Cannabis Ubiquitin promoter sequence to a suitable reporter gene; e.g., dsRED; 2) transforming a chimeric Cannabis Ubiquitin promoter:reporter gene expression cassette into a Cannabis plant for expression of the promoter; and 3) testing for expression of the Cannabis Ubiquitin promoter in various cell types of transgenic plant tissues, e.g., leaves, roots, flowers, seeds, transformed with the chimeric Cannabis Ubiquitin promoter:reporter gene expression cassette by assaying for expression of the reporter gene product.

In another embodiment, a recombinant DNA construct comprising at least one heterologous nucleic acid fragment operably linked to any promoter, or combination of promoter elements, is provided. Recombinant DNA constructs can be constructed by operably linking the nucleic acid fragment of the Cannabis Ubiquitin promoter or a fragment that is substantially similar and functionally equivalent to any portion of the nucleotide sequence set forth in SEQ ID NO: 3 to a heterologous nucleic acid fragment. Any heterologous nucleic acid fragment can be used to practice the invention. The selection will depend upon the desired application or phenotype to be achieved. The various nucleic acid sequences can be manipulated so as to provide for the nucleic acid sequences in the proper orientation. It is believed that various combinations of promoter elements as described herein may be useful in practicing the present invention.

In another embodiment, host cells comprising either the recombinant DNA constructs of the invention as described herein or isolated polynucleotides of the invention are provided. Examples of host cells which can be used to practice the invention include, but are not limited to, yeast, bacteria, and plants.

Plasmid vectors comprising the instant recombinant expression construct can be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene. Aspects of the present disclosure include a recombinant expression vector comprising a nucleic acid that includes the Cannabis Ubiquitin promoter. Suitable expression vectors include vectors comprising a nucleotide sequence that encodes an RNA (e.g., an mRNA) that when transcribed from the polynucleotides of the vector will result in the expression of a subject gene product. In some cases, the gene product is a polypeptide.

Suitable methods for transformation of plants include any method by which DNA can be introduced into a cell, for example and without limitation: electroporation (see, e.g., U.S. Pat. No. 5,384,253); micro-projectile bombardment (see, e.g., U.S. Pat. Nos. 5,015,580, 5,550,318, 5,538,880, 6,160,208, 6,399,861, and 6,403,865); Agrobacterium-mediated transformation (see, e.g., U.S. Pat. Nos. 5,635,055, 5,824,877, 5,591,616; 5,981,840, and 6,384,301); protoplast transformation (see, e.g., U.S. Pat. No. 5,508,184); non-Agrobacterium bacteria or viruses such as Rhizobium sp. NGR234, Sinorhizoboium meliloti, Mesorhizobium loti, potato virus X, cauliflower mosaic virus and cassava vein mosaic virus and/or tobacco mosaic virus, See, e.g., Chung et al. (2006) Trends Plant Sci. 11(1):1-4. Methods for transforming dicots, primarily by use of Agrobacterium tumefaciens, and obtaining transgenic plants have been published, among others, for cotton (U.S. Pat. Nos. 5,004,863, 5,159,135); soybean (U.S. Pat. Nos. 5,569,834, 5,416,011); Brassica (U.S. Pat. No. 5,463,174); peanut (Cheng et al., Plant Cell Rep. 15:653-657 (1996), McKently et al., Plant Cell Rep. 14:699-703 (1995)); papaya (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses Agrobacterium rhizogenes (Tepfler, M. and Casse-Delbart, F., Microbiol. Sci. 4:24-28 (1987)). Transformation of soybeans using direct delivery of DNA has been published using PEG fusion (PCT Publication No. WO 92/17598), electroporation (Chowrira et al., Mol. Biotechnol. 3:17-23 (1995); Christou et al., Proc. Natl. Acad. Sci. U.S.A. 84:3962-3966 (1987)), microinjection, or particle bombardment (McCabe et al., Biotechnology 6:923-

926 (1988); Christou et al., Plant Physiol. 87:671-674 (1988)). A skilled artisan can easily use known transformations known in the art for transforming dicots for transforming Cannabis plants.

In addition to direct transformation of a particular plant genotype with a construct prepared according to the current invention, transgenic plants may be made by crossing a plant having a selected DNA of the invention to a second plant lacking the construct. Therefore, the current invention not only encompasses a plant directly transformed or regenerated from cells which have been transformed in accordance with the current invention, but also the progeny of such plants.

There are a variety of methods for the regeneration of plants from plant tissues. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, Calif., 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

Skilled artisans are further familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook, J. et al., In Molecular Cloning: A Laboratory Manual; 2.sup.nd ed.; Cold Spring Harbor Laboratory Press: Cold Spring Harbor, N.Y., 1989; Maliga et al., In Methods in Plant Molecular Biology; Cold Spring Harbor Press, 1995; Birren et al., In Genome Analysis: Detecting Genes, 1; Cold Spring Harbor: New York, 1998; Birren et al., In Genome Analysis: Analyzing DNA, 2; Cold Spring Harbor: New York, 1998; Clark, Ed., In Plant Molecular Biology: A Laboratory Manual; Springer: New York, 1997).

The skilled artisan will also recognize that different independent transformation events will result in different levels and patterns of expression of the chimeric genes (Jones et al., EMBO J. 4:2411-2418 (1985); De Almeida et al., Mol. Gen. Genetics 218:78-86 (1989)). Thus, multiple events must be screened in order to obtain lines displaying the desired expression level and pattern. Such screening may be accomplished by Northern analysis of mRNA expression, Western analysis of protein expression, or phenotypic analysis. Also of interest are seeds obtained from transformed plants displaying the desired gene expression profile.

Cells that survive exposure to a selective agent, or cells that have been scored positive in a screening assay, may be cultured in media that supports regeneration of plants. In an embodiment, any suitable plant tissue culture media may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the .beta.-glucuronidase, luciferase, or green fluorescent protein genes) that may be present on the recombinant nucleic acid constructs. Such selection and screening methodologies are well known to those skilled in the art. Molecular confirmation methods that can be used to identify transgenic plants are known to those with skill in the art. Several exemplary methods are further described below.

In an embodiment, a method of expressing at least one transgene is provided that includes (a) transforming a cell of the plant with a recombinant DNA construct comprising a polynucleotide sequence having at least 90% sequence identity to SEQ ID NO:3, (b) growing fertile mature plants from the transformed plant cell of step (a); and (c) selecting plants containing the transformed plant cell wherein the expression of the heterologous nucleic acid fragment is increased in the number of cells of the plant. In an embodiment, the nucleotide sequence is operably linked to at least one heterologous polynucleotide sequence to be expressed.

Heterologous Gene Expression in Cannabis

The promoter sequences and methods disclosed herein are useful in regulating expression of any heterologous nucleotide sequence in a host plant. Thus, the heterologous nucleotide sequence operably linked to the promoters disclosed herein may be a structural gene encoding a protein of interest. Various changes in phenotype are of interest including, but not limited to, modifying the fatty acid composition in a plant, altering the amino acid content of a plant, altering a plant's pathogen defense mechanism, introducing gene editing platforms, etc. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Trichome specific promoters of the present technology may also be used for expressing a nucleic acid that will decrease or inhibit expression of a native gene in the plant. Such nucleic acids may encode antisense nucleic acids, ribozymes, sense suppression agents, or other products that inhibit expression of a native gene. The trichome specific promoters of the present technology may also be used to express proteins or peptides in "molecular farming" applications. Such proteins or peptides include but are not limited to industrial enzymes, antibodies, therapeutic agents, and nutritional products.

Genes of interest are reflective of the commercial markets and interests of those involved in the development of the plant. Crops and markets of interest change, and as developing nations open up world markets, new crops and technologies will emerge also. In addition, as our understanding of agronomic characteristics and traits such as yield and heterosis increase, the choice of genes for transformation will change accordingly. General categories of genes of interest include, but are not limited to, those genes involved in information, such as zinc fingers, those involved in communication, such as kinases, and those involved in housekeeping, such as heat shock proteins. More specific categories of transgenes, for example, include, but are not limited to, genes encoding important traits for agronomics, insect resistance, disease resistance, herbicide resistance, sterility, cannabinoid synthesis, grain or seed characteristics, ability to resist cold, heat, and drought, and commercial products. Genes of interest include, generally, those involved in oil, starch, carbohydrate, or nutrient metabolism as well as those affecting seed size, plant development, plant growth regulation, and yield improvement. Plant development and growth regulation also refer to the development and growth regulation of various parts of a plant, such as the flower, seed, root, leaf and shoot.

Disease and/or insect resistance genes may encode resistance to pests that have great yield drag such as for example, anthracnose, soybean mosaic virus, soybean cyst nematode, root-knot nematode, brown leaf spot, Downy mildew, purple seed stain, seed decay and seedling diseases caused commonly by the fungi—*Pythium* sp., *Phytophthora* sp., *Rhizoctonia* sp., *Diaporthe* sp. Bacterial blight caused by the bacterium *Pseudomonas syringae* pv. Glycinea. Genes conferring insect resistance include, for example, *Bacillus thuringiensis* toxic protein genes (U.S. Pat. Nos. 5,366,892; 5,747,450; 5,737,514; 5,723,756; 5,593,881; and Geiser et al (1986) Gene 48:109); lectins (Van Damme et al. (1994) Plant Mol. Biol. 24:825); and the like.

Herbicide resistance traits may include genes coding for resistance to herbicides that act to inhibit the action of acetolactate synthase (ALS), in particular the sulfonylurea-type herbicides (e.g., the acetolactate synthase ALS gene containing mutations leading to such resistance, in particular the S4 and/or HRA mutations). The ALS-gene mutants encode resistance to the herbicide chlorsulfuron. Glyphosate acetyl transferase (GAT) is an N-acetyltransferase from *Bacillus licheniformis* that was optimized by gene shuffling for acetylation of the broad spectrum herbicide, glyphosate, forming the basis of a novel mechanism of glyphosate tolerance in transgenic plants (Castle et al. (2004) Science 304, 1151-1154).

Antibiotic resistance genes include, for example, neomycin phosphotransferase (npt) and hygromycin phosphotransferase (hpt). Two neomycin phosphotransferase genes are used in selection of transformed organisms: the neomycin phosphotransferase I (nptI) gene and the neomycin phosphotransferase II (npII) gene. The second one is more widely used. It was initially isolated from the transposon Tn5 that was present in the bacterium strain Escherichia coli K12. The gene codes for the aminoglycoside 3'-phosphotransferase (denoted aph(3')-II or NPTII) enzyme, which inactivates by phosphorylation a range of aminoglycoside antibiotics such as kanamycin, neomycin, geneticin and paromomycin. NPTII is widely used as a selectable marker for plant transformation. It is also used in gene expression and regulation studies in different organisms in part because N-terminal fusions can be constructed that retain enzyme activity. NPTII protein activity can be detected by enzymatic assay. In other detection methods, the modified substrates, the phosphorylated antibiotics, are detected by thin-layer chromatography, dot-blot analysis or polyacrylamide gel electrophoresis. Plants such as maize, cotton, tobacco, Arabidopsis, flax, soybean and many others have been successfully transformed with the nptII gene.

The CRISPR (Clustered Regularly Interspaced Short Palindromic Repeats)/Cas (CRISPR Associated) nuclease system is a recently engineered nuclease system based on a bacterial system that can be used for genome engineering and used with the Cannabis Ubiquitin promoter identified herein. It is based on part of the adaptive immune response of many bacteria and Archaea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer." Cas9 cleaves the DNA to generate blunt ends at the double-stranded break (DSB) at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et al., (2012) Science 337, pp. 816-821, Jinek et al., (2013), eLife 2:e00471, and David Segal, (2013) eLife 2:e00563). In other examples, the crRNA associates with the tracrRNA to guide the Cpf1 nuclease to a region homologous to the crRNA to cleave DNA with staggered ends (see Zetsche, Bernd, et al. Cell 163.3 (2015): 759-771.). Thus, the CRISPR/Cas system can be engineered to create a DSB at a desired target in a genome, and repair of the DSB can be influenced by the use of repair inhibitors to cause an increase in error prone repair.

Genes involved in plant growth and development have been identified in plants. One such gene, which is involved in cytokinin biosynthesis, is isopentenyl transferase (IPT). Cytokinin plays a critical role in plant growth and development by stimulating cell division and cell differentiation (Sun et al. (2003), Plant Physiol. 131: 167-176).

Calcium-dependent protein kinases (CDPK), a family of serine-threonine kinase found primarily in the plant kingdom, are likely to function as sensor molecules in calcium-mediated signaling pathways. Calcium ions are important second messengers during plant growth and development (Harper et al. Science 252, 951-954 (1993); Roberts et al. Curr. Opin. Cell Biol. 5, 242-246 (1993); Roberts et al. Annu. Rev. Plant Mol. Biol. 43, 375-414 (1992)).

The quality of seeds and grains is reflected in traits such as levels and types of fatty acids or oils, saturated and unsaturated, quality and quantity of essential amino acids, and levels of carbohydrates. Therefore, commercial traits can also be encoded on a gene or genes that could increase for example methionine and cysteine, two sulfur containing amino acids that are present in low amounts in soybeans. Cystathionine gamma synthase (CGS) and serine acetyl transferase (SAT) are proteins involved in the synthesis of methionine and cysteine, respectively.

In some embodiments, transformation of a recipient cell with more than one advantageous transgene is described. Two or more transgenes can be supplied in a single transformation event using either distinct transgene-encoding vectors, or a single vector incorporating two or more gene coding sequences. Any two or more transgenes of any description, such as those conferring herbicide, insect, disease (viral, bacterial, fungal, and nematode), or drought resistance, oil quantity and quality, or those increasing yield or nutritional quality may be employed as desired.

Kits

Further aspects of the present disclosure include a kit that includes a recombinant expression vector, as described above, comprising the subject nucleic acid, i.e., a nucleic acid comprising a Cannabis Ubiquitin promoter wherein the promoter comprises a nucleotide sequence having at least 90% sequence identity to the nucleotide sequence set forth in SEQ ID NO: 1. In certain embodiments, the recombinant expression vector of the subject kit comprises multiple cloning sites, or equivalents thereof, that facilitate subcloning a nucleotide sequence encoding a gene product of interest to a user into the recombinant expression vector, thereby operably linking the nucleotide sequence encoding the heterologous gene product of interest to the Cannabis Ubiquitin promoter. In certain embodiments, the recombinant expression vector of the subject kit comprises a nucleotide sequence encoding fluorescent protein operably linked to the Cannabis promoter.

The kit may also include a control expression vector, such as a positive control expression vector and/or a negative control expression vector. In some embodiments, the positive control expression vector comprises a nucleic acid encoding a known gene product, such as a fluorescent polypeptide as described above, operably linked to the Cannabis promoter. In some instances, the positive control expression vector contains a nucleic acid encoding a fluorescent protein, such as a green fluorescent protein, a yellow fluorescent protein, or a red fluorescent protein.

EXAMPLES

Aspects of the present teachings can be further understood in light of the following examples, which should not be construed as limiting the scope of the present teachings in any way.

The practice of the present teachings employ, unless otherwise indicated, conventional methods of protein chemistry, biochemistry, recombinant DNA techniques and pharmacology, within the skill of the art. Such techniques are explained fully in the literature. See, e.g., T. Creighton, Proteins: Structures and Molecular Properties, 1993, W. Freeman and Co.; A. Lehninger, Biochemistry, Worth Publishers, Inc. (current addition); J. Sambrook et al., Molecular Cloning: A Laboratory Manual, 2nd Edition, 1989; Methods In Enzymology, S. Colowick and N. Kaplan, eds., Academic Press, Inc.; Remington's Pharmaceutical Sciences, 18th Edition, 1990, Mack Publishing Company, Easton, Pa.; Carey and Sundberg, Advanced Organic Chemistry, Vols. A and B, 3rd Edition, 1992, Plenum Press.

The practice of the present teachings also employ, unless otherwise indicated, conventional methods of statistical analysis, within the skill of the art. Such techniques are explained fully in the literature. See, e.g., J. Little and D. Rubin, Statistical Analysis with Missing Data, 2nd Edition 2002, John Wiley and Sons, Inc., NJ; M. Pepe, The Statistical Evaluation of Medical Tests for Classification and Prediction (Oxford Statistical Science Series) 2003, Oxford University Press, Oxford, UK; X. Zhoue et al., Statistical Methods in Diagnostic Medicine 2002, John Wiley and Sons, Inc., NJ; T. Hastie et. al, The Elements of Statistical Learning: Data Mining, Inference, and Prediction, Second Edition 2009, Springer, N.Y.; W. Cooley and P. Lohnes, Multivariate procedures for the behavioral science 1962, John Wiley and Sons, Inc. NY; E. Jackson, A User's Guide to Principal Components 2003, John Wiley and Sons, Inc., NY.

Example 1-Identification of Cannabis Ubiquitin Promoter

Ubiquitin promoters enable constitutive and whole plant expression of foreign or native genes without inducing gene silencing that occurs with viral promoters. Ubiquitin gene sequences from Arabidopsis, Lettuce, and Lotus were used to create a sequence (SEQ ID NO: 1) for BLAST analysis against Phylos' cannabis reference genome to discover a Cannabis homolog.

Identification of Cannabis Promoter Sequence

FIG. 1 illustrates the ubiquitin gene structure from Lotus, demonstrating a 5' UTR with a small UTR exon and intron. Further shown is the CAAG/gta-cag/ATC splice site. See, MPMI Vol. 21, No. 4, 2008, pp. 375-382. doi:10.1094/MPMI -21-4-0375. © 2008 The American Phytopathological Society.

One sequence hit from the cannabis reference genome demonstrated the proper 5' UTR region with proper number of five Ubiquitin repeats. SEQ ID NO:2 is the identified Cannabis Ubiquitin protein sequence. SEQ ID NO:3 is the polynucleotide genomic DNA sequence of the Cannabis Ubiquitin promoter that was cloned from genomic Cannabis DNA.

The Ubiquitin terminator sequence was also cloned from Cannabis genomic DNA for use in subsequent proof of concept experiments, and is identified as SEQ ID NO:4.

Table 1 describes the Ubiquitin promoter sequences that were used to BLAST the Cannabis genome (SEQ ID NO:1) and the resulting Cannabis Ubiquitin discovered sequence (SEQ ID NO:2). The sequences contains one letter codes for nucleotide sequence characters and the single and three letter codes for amino acids as defined in the IUPAC-IUB standards described in Nucleic Acids Research 13:3021-3030 (1985) and in the Biochemical Journal 219(2):345-373 (1984).

TABLE 1

| Ubiquitin sequences | |
|---|---|
| SEQ ID NO:1 | MQIFVKTLTGKTITLEVESSDTIDN VKAKIQDKEGIPPDQQRLIFAGKQL EDGRTLADYNIQKESTLHLVLRLRG GMQIFVKTLTGKTITLEVESSDTID NVKAKIQDKEGIPPDQQRLIFAGKQ LEDGRTLADYNIQKESTLHLVLRLR GGMQIFVKTLTGKTITLEVESSDTI DNVKAKIQDKEGIPPDQQRLIFAGK QLEDGRTLADYNIQKESTLHLVLRL RGGMQIFVKTLTGKTITLEVESSDT IDNVKAKIQDKEGIPPDQQRLIFAG KQLEDGRTLADYNIQKESTLHLVLR LRGGMQIFVKTLTGKTITLEVESSD TIDNVKAKIQDKEGIPPDQQRLIFA GKQLEDGRTLADYNIQKESTLHLVL RLRGGMQIFVKTLTGKTITLEVESS DTIDNVKAKIQDKEGIPPDQQRLIF AGKQLEDGRTLADYNIQKESTLHLV LRLRGGF |
| SEQ ID NO: 2 | MQIFVKTLTGKTITLEVESSDTIDN VKAKIQDKEGIPPDQQRLIFAGKQL EDGRTLADYNIQKESTLHLVLRLRG GMQIFVKTLTGKTITLEVESSDTID NVKAKIQDKEGIPPDQQRLIFAGKQ |

TABLE 1-continued

Ubiquitin sequences

| | |
|---|---|
| | LEDGRTLADYNIQKESTLHLVLRLR GGMQIFVKTLTGKTITLEVESSDTI DNVKAKIQDKEGIPPDQQRLIFAGK QLEDGRTLADYNIQKESTLHLVLRL RGGMQIFVKTLTGKTITLEVESSDT IDNVKAKIQDKEGIPPDQQRLIFAG KQLEDGRTLADYNIQKESTLHLVLR LRGGMQIFVKTLTGKTITLEVESSD TIDNVKAKIQDKEGIPPDQQRLIFA GKQLEDGRTLADYNIQKESTLHLVL RLRGGF |
| SEQ ID NO: 3 | GAATTCAAAGTCTTGCAGTGTAATT ACGGGTTGAAAAATTACAAAATCCG CATATGCAGTTTGATTTGAAAAAGT AGTCTAAACTCACACCACTCGCACA CTCATATCCAAAACAAAGACACCAA ATCCAAACCCAAATCTAGATAGAAA TTGAATCATATTTAGATCAAAAGGG AACATAGACCCGACTTTAGACCGCA AAACCGGCCAAGTCCTAGGTCAACA TCCGGGTCACGGTCCTAGTCCGAGT CTAAGTTTGGGTGGGTGGGTCCATA GCTTTTTTTTTTTTTTTTTTTGAAT AAAGATAAACTTCATTAACTCATGA GCAATCGCTCAAAAGTACAACTTTA AGTTCCGAAGGGATATCATCCTTCG TGAACATACGATCAGCAAATAATCG AGACTGACGTGCAACCACATGTGCG GCTCGATTAGCAGAACGTTTAACAA ACCTAATATTCCAAATTTTGTGTGT AAGTGGAAGCTGTGGAGTGTACGGC ACGTCATGTTAATAGGTGGCGTAAT AGAATTGGAAATCCTAATCAATGGG TTTCGTTTTGCCCTCACCATATAAA TACCCTCTTATCCTTCATTTCTATT CATTACTACTTTCTAAGCGATTCTC ACAATAATCTCTGCCCCCATATCAA AATTCCCAAGAACAACCCTAATCCC TTCTCTTCGTACACTCGTTCAAGGT AATCAAATTCTTGCTTCCTTAGTCA AAAATTGCTTCTGATCATAGAACACT CGTATATTTGATTTTTTTTTTTGG AATTATATATATGTTTTTTTATAT TATTGAATTTCTTTAGGGTTTTTAA TTTTCGTCTTATCTTTGAATCAACC GAATAATTTTTGAAAAGTAATGTAC TTTTTGTTCATCTGCTAATTTAACT TGTATCGTATCTTTGAATTTTGTTA GAGTATTTAATTCTCGACCTGTTTG TATTTAATTTTTAAATTTTACCGA ATAATTTTTGGAAAATTATACTTCT TTTTTCATCTGTGAAATGTATCAAT AATATTGGGTTTCATACAATTTTAG GGTTTTATTATTTAATCAGGCAAGA TTGTTTTTTTTTTTCTTTTAAATTC TAAAGAAGTTTTGTCTGAAATTATT TTTTTTTGGGGATAAATTCTGATG AGATTTTGGTTTAATTGTGTAATTT TAG |
| SEQ ID NO: 4 | ATCTGTTTATAGCTGTTATGAATGG AATGCATTTTATTGTTATGTTTATG GTTTTTATTACTATGAAACAAACTG CTTTTATGATTTAGTATGGTTAATG GTTTTTAAAACTTGTTATATATGAC AGTTTATGGTTTGGCCTTGTGGTGG TATATTTTCATATTCAGAGTGAGAA ATTCTTTCTCATGTTTATGTTCTTG AGTTGTTTTTAATTTGTTGGTTTTA TTAATATCAAGGTTTTAGGCTCAAC TCGTATATGAAGGTCTGAATCTAAT TATTGTTGCTCTATAGAATTTTCCT CTGGCCAGGTTTTAATGGAGTTTAA TCACACACACCAATTACATGGAACT TGATTATGCATTCTACTCTACACAT ATCAGAATTATTACTTCATCATCCA AGTATGGACTTATATGAAAATTGAT |

TABLE 1-continued

Ubiquitin sequences

| | |
|---|---|
| | ATAAAATATGAAGGTTATACTTCTA TTGCACCAGTATTGTATTACCTTCA TTATAAGTCAAGAGAAATTTTTTGT GTCAATTATAGAGTTGGGGAGAAAT TGGGCTTTGTTGCAAGCAAAAAAGT GAAAACTAATTTAGTTTCTAGAGGA AGAAGAACAAATATAAATAAATTTA TTTTACTTCAACTTAGTTTATATGT ATATGTATATTTATCCTAGCCGTCT CTAGTTTTTACAAGGCTTTGGACAA AATTAAAAAGTATTATTTTACAAAT ACATAAAAATAATATGTTTTTTTTT TTTTTTATAAAAGTACAGTTGTTGT GGTACC |

Construction of dsRED Reporter

Proof of was established using a dsRED reporter construct. Genomic DNA was isolated using Plant DNA easy. The coding region for DsRED protein was isolated from base DsRED expression vector. The putative Cannabis Ubiquitin promoter, DsRED fragment and terminator were cloned into the pUC19 base vector. The steps included digesting pUC19 with EcoR1 and Kpnl and gel purifying the fragment, amplifying the CsuBQ promoter, CsUBQ Terminator and DsRED coding regions.

Gibson cloning/PCR was used to assemble the CsUBQ promoter/DsRED/CsUBQ terminator of promoter and terminator sequences into pUC19. The following primers were used for Gibson fragment assembly:

```
Cannabis ubiquitin promoter
forward primer-
                                       SEQ ID NO: 5
CGACGTTGTAAAACGACGGCCAGTG

AATTCAAAGTCTTGCAGTGTAATTAC

Cannabis ubiquitin promoter
reverse primer-
                                       SEQ ID NO: 6
GCGCGCCATCATCTAAAATTACACAAT

TAAACCAAAATC dsRED forward primer
                                       SEQ ID NO: 7
TGTGTAATTTTAGATGATGGCGCGCTCCTCC dsRED reverse primer-
                                       SEQ ID NO: 8
GCTATAAACAGATCTACAGGAACAGGTGGTGGC cannabis ubiquitin terminator
forward primer-
                                       SEQ ID NO: 9
CTGTTCCTGTAGATCTGTTTATAGCTGTTATGAATG cannabis ubiquitin terminator
reverse primer-
                                       SEQ ID NO: 10
TCGACTCTAGAGGATCCCCGGGTACCAC

AACAACTGTACTTTTATAAAAAAAAAAAAAAC
```

Figure 2:
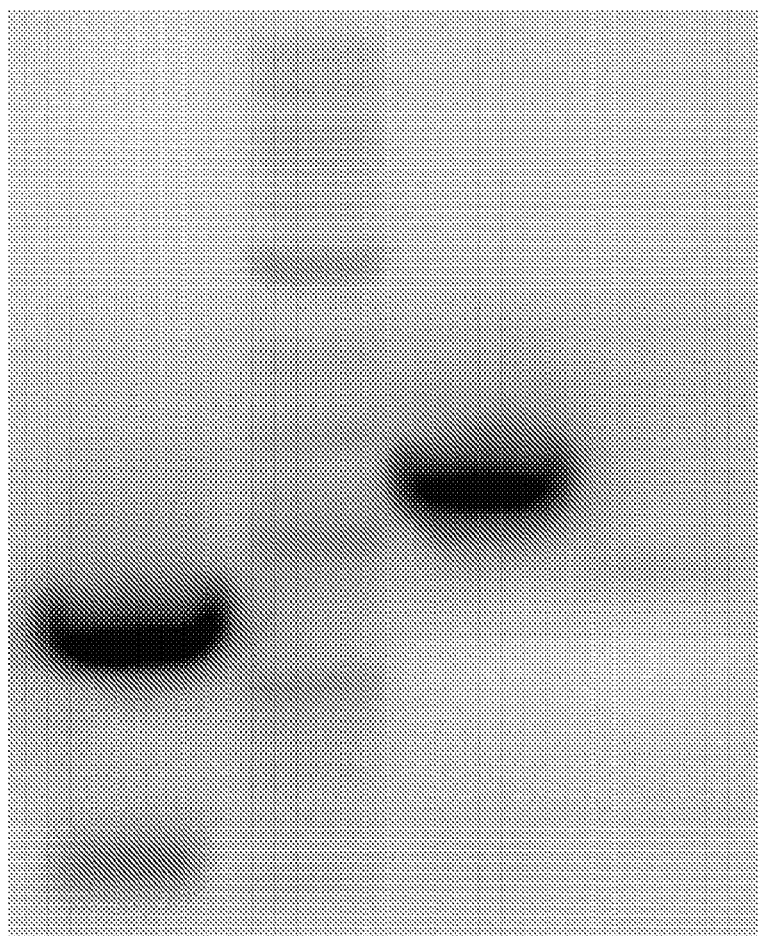
FIG. 2 illustrates presence of promoter and terminator sequences in dsRED reporter construct.

FIG. 2 illustrates the presence of each component.

The following amounts of DNA were acquired for a Gibson Assembly reaction:

| | | |
|---|---|---|
| pUC19 Kpnl/EcoRI Fragment | 67 ng/ul = | 0.04145 pmol/ul |
| CannabisUBQ Promoter Fragment | 137 ng/ul = | 0.188 pmol/ul |

-continued

| | | |
|---|---|---|
| dsRed ORF Fragment | 184 ng/ul = | 0.435 pmol/ul |
| CannabisUBQ Terminator | 6 ng/ul = | 0.013 pmol/ul |

Gibson assembly reaction was used according to manufacturer's recommendation and transformed into NEB 10-Beta cells, and plated on Amp50 plates.

Proof of Concept

The Cannabis dsRED reporter construct was tested for proof of concept using lettuce leaf protoplasts. Inner lettuce leaf tissue was removed and dissolved in 10% bleach plus 20 ul tween20. Lettuce tissue was placed in a petri dish with 35 ml PG solution (300 mM Sorbitol, 2.5% PVP10, and 10 mM CaCL2, ph 5.8). Enzyme mix to release protoplasts (20 mM MES pH5.7, 4% (v/v) Viscozyme, 2% (v/v) Pectinase, 10 mM CaCl2, 13.7% (w/v) Sucrose) was made and filter sterilized. The tissue was vacuum infiltrated for 15 minutes and then left at RT overnight (~16 hr) to digest. Next, 10 ml of 16% sucrose was added and placed on an orbital shaker for 1 hour at 70RPM. Following filtering through 70 um mesh into a 50 ml tube, the mixture was transferred~8 ml to round bottom tubes. After overlaying 1 ml of W5 medi (fresh filter sterile), the tubes were left for 1 hour then spun 100 g for 10 minutes to isolate viable protoplasts. The green cell layer was removed at the interface of W5, the enzyme was mixed into 2 tubes and then washed with 9 ml of W5 (added to each tube, capped and inverted 2x) and spun at 100 g for 8 minutes. After removing the wash solution, the pellets of cells were resuspended in 1 ml of W5. Removed a small amount to count cells and check viability with FDA/PI stain. Each 14 ml round bottom tube had 25 ul (10 ug) of plasmid placed within the tube. 200 ul of cells were added and mixed. 230 ul of fresh 40% PEG4000 solution (0.1M CalCl2, 0.2M Mannitol, 4 g/10 ml PEG4000) was then added. After gentle mixing the tubes were incubated at RT for 10 minutes. To stop the transfection, 9 ml of W5 solution was added and the cells were spun for 10 minutes at 100 g. The solution was removed from the cells and then resuspended in 500 ul WI solution. The cells were left to incubate overnight to express DsRED protein.

Figure 3:
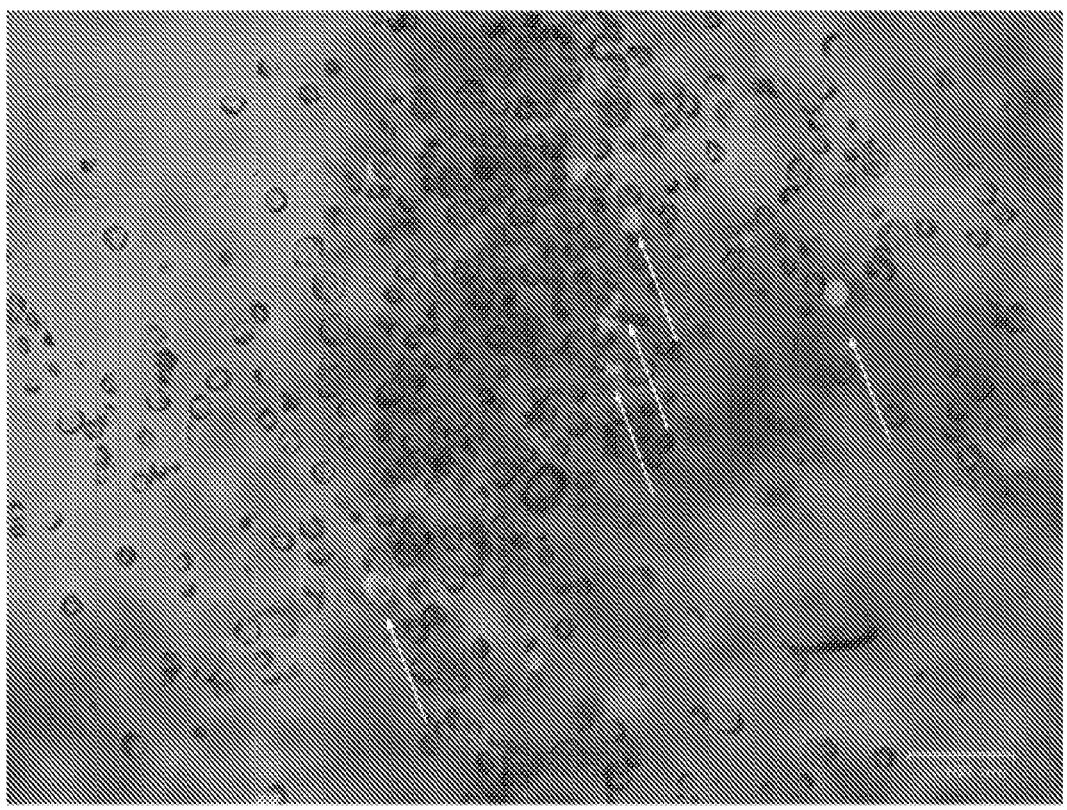
FIG. 3 illustrates a control proof of concept promoter using a Lotus promoter dsRED reporter construct (LjUBQ-DsRED) in lettuce. The arrows point to representative cells expressing the reporter construct.
Figure 4A:
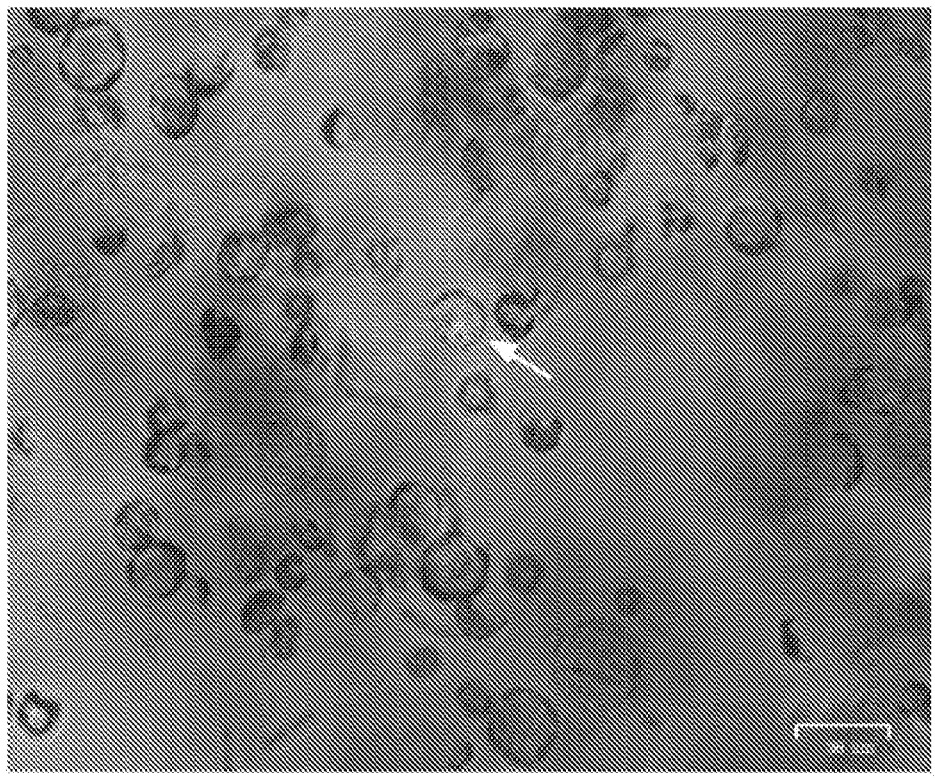
FIG. 4A is a standard view.
Figure 4B:
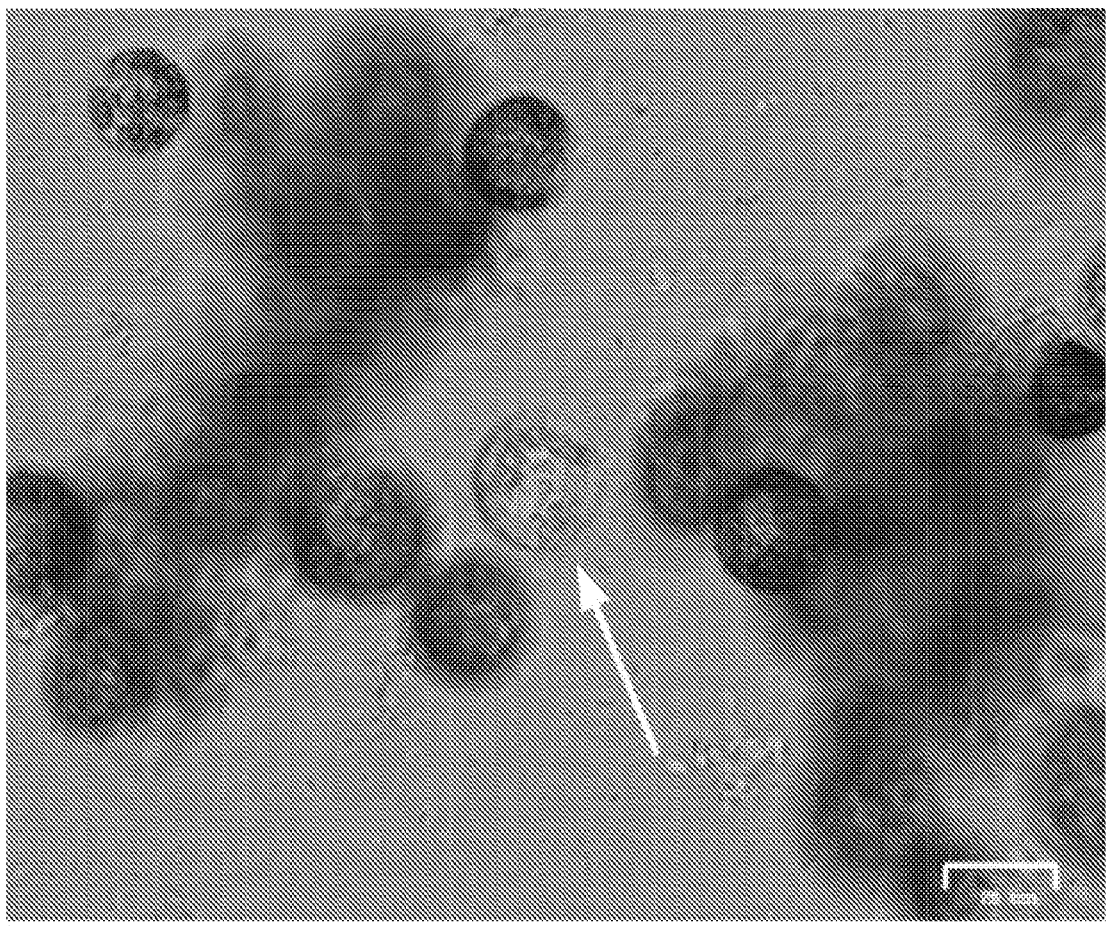
FIG. 4B is a close up view. Each arrow points to cell expressing the reporter construct.

FIG. 3 illustrates a control lettuce protoplast expressing dsRED using a LjUBQ-DsRED construct after 48 hours incubation. FIG. 4 illustrates lettuce protoplast expressing dsRED using a Cannabis ubiquitin protomer (CdUBQ-DsRED) at 48 hours. These results provide a proof of concept that a unique Cannabis promoter can be used to drive reporter expression in sample (lettuce) protoplast cells.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

What is claimed is:

1. A recombinant DNA vector comprising a promoter comprising SEQ ID NO: 3.

2. The vector of claim 1, wherein the promoter is operably linked to at least one heterologous coding sequence or functional RNA.

3. The vector of claim 2, further comprising a polynucleotide sequence encoding a selectable marker.

4. The vector of claim 2, further comprising a 3' untranslated polynucleotide sequence, a 5' untranslated polynucleotide sequence, or both.

5. The vector of claim 2, further comprising one or more intron polynucleotide sequences.

6. The vector of claim 2, wherein the at least one heterologous coding sequence or functional RNA is a Cannabis coding sequence or functional RNA.

7. The vector of claim 2, wherein the at least one heterologous coding sequence encodes a protein selected from the group consisting of: a reporter protein, a selection marker, a protein conferring disease resistance, a protein conferring herbicide resistance, a protein conferring insect resistance, a gene editing protein, a protein involved in carbohydrate metabolism, a protein involved in fatty acid metabolism, a protein involved in amino acid metabolism, a protein involved in plant or tissue development, a protein involved in plant growth regulation, a protein involved in yield improvement, a protein involved in drought resistance, a protein involved in cold resistance, a protein involved in heat resistance, and a protein involved in salt resistance in plants.

8. A plant cell comprising a recombinant DNA vector comprising a promoter comprising SEQ ID NO: 3.

9. The plant cell of claim 8, wherein the promoter is operably linked to at least one heterologous coding sequence or functional RNA.

10. The plant cell of claim 9, wherein the vector further comprises a polynucleotide sequence encoding a selectable marker.

11. The plant cell of claim 9, wherein the vector further comprises a 3' untranslated polynucleotide sequence, a 5' untranslated polynucleotide sequence, or both.

12. The plant cell of claim 9, wherein the vector further comprises one or more intron polynucleotide sequences.

13. The plant cell of claim 9, wherein the at least one heterologous coding sequence or functional RNA is a Cannabis coding sequence or functional RNA.

14. The plant cell of claim 9, wherein the at least one heterologous coding sequence encodes a protein selected from the group consisting of: a reporter protein, a selection marker, a protein conferring disease resistance, a protein conferring herbicide resistance, a protein conferring insect resistance, a gene editing protein, a protein involved in carbohydrate metabolism, a protein involved in fatty acid metabolism, a protein involved in amino acid metabolism, a protein involved in plant or tissue development, a protein involved in plant growth regulation, a protein involved in yield improvement, a protein involved in drought resistance, a protein involved in cold resistance, a protein involved in heat resistance, and a protein involved in salt resistance in plants.

15. The plant cell of claim 8, wherein the plant cell is a *Cannabis* plant cell.

16. The plant cell of claim 8, wherein the plant cell is a *Cannabis sativa* cell.

17. The vector of claim 1, wherein the promoter is operably linked to a heterologous gene.

18. The vector of claim 1, wherein the promoter is operably linked to a heterologous *Cannabis sativa* gene.

19. The vector of claim 1, wherein the vector is a plasmid vector.

20. A *Cannabis sativa* cell comprising a recombinant DNA vector, wherein the vector comprises a promoter comprising SEQ ID NO: 3 operably linked to a heterologous *Cannabis sativa* gene.

* * * * *

SEQUENCE LISTING

```
<160> NUMBER OF SEQ ID NOS: 10

<210> SEQ ID NO 1
<211> LENGTH: 457
<212> TYPE: PRT
<213> ORGANISM: Cannabis sativa

<400> SEQUENCE: 1

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160
```

-continued

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ala Asp Tyr Asn Ile Gln Lys Glu Ser Thr Leu His Leu Val Leu Arg
    210                 215                 220

Leu Arg Gly Gly Met Gln Ile Phe Val Lys Thr Leu Thr Gly Lys Thr
225                 230                 235                 240

Ile Thr Leu Glu Val Glu Ser Ser Asp Thr Ile Asp Asn Val Lys Ala
                245                 250                 255

Lys Ile Gln Asp Lys Glu Gly Ile Pro Pro Asp Gln Gln Arg Leu Ile
            260                 265                 270

Phe Ala Gly Lys Gln Leu Glu Asp Gly Arg Thr Leu Ala Asp Tyr Asn
        275                 280                 285

Ile Gln Lys Glu Ser Thr Leu His Leu Val Leu Arg Leu Arg Gly Gly
    290                 295                 300

Met Gln Ile Phe Val Lys Thr Leu Thr Gly Lys Thr Ile Thr Leu Glu
305                 310                 315                 320

Val Glu Ser Ser Asp Thr Ile Asp Asn Val Lys Ala Lys Ile Gln Asp
                325                 330                 335

Lys Glu Gly Ile Pro Pro Asp Gln Gln Arg Leu Ile Phe Ala Gly Lys
            340                 345                 350

Gln Leu Glu Asp Gly Arg Thr Leu Ala Asp Tyr Asn Ile Gln Lys Glu
        355                 360                 365

Ser Thr Leu His Leu Val Leu Arg Leu Arg Gly Gly Met Gln Ile Phe
    370                 375                 380

Val Lys Thr Leu Thr Gly Lys Thr Ile Thr Leu Glu Val Glu Ser Ser
385                 390                 395                 400

Asp Thr Ile Asp Asn Val Lys Ala Lys Ile Gln Asp Lys Glu Gly Ile
                405                 410                 415

Pro Pro Asp Gln Gln Arg Leu Ile Phe Ala Gly Lys Gln Leu Glu Asp
            420                 425                 430

Gly Arg Thr Leu Ala Asp Tyr Asn Ile Gln Lys Glu Ser Thr Leu His
        435                 440                 445

Leu Val Leu Arg Leu Arg Gly Gly Phe
    450                 455

<210> SEQ ID NO 2
<211> LENGTH: 381
<212> TYPE: PRT
<213> ORGANISM: Cannabis sativa

<400> SEQUENCE: 2

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

```
Ser Thr Leu His Leu Val Leu Arg Leu Arg Gly Gly Met Gln Ile Phe
 65                  70                  75                  80

Val Lys Thr Leu Thr Gly Lys Thr Ile Thr Leu Glu Val Glu Ser Ser
                 85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205

Ala Asp Tyr Asn Ile Gln Lys Glu Ser Thr Leu His Leu Val Leu Arg
210                 215                 220

Leu Arg Gly Gly Met Gln Ile Phe Val Lys Thr Leu Thr Gly Lys Thr
225                 230                 235                 240

Ile Thr Leu Glu Val Glu Ser Ser Asp Thr Ile Asp Asn Val Lys Ala
                245                 250                 255

Lys Ile Gln Asp Lys Glu Gly Ile Pro Pro Asp Gln Gln Arg Leu Ile
            260                 265                 270

Phe Ala Gly Lys Gln Leu Glu Asp Gly Arg Thr Leu Ala Asp Tyr Asn
        275                 280                 285

Ile Gln Lys Glu Ser Thr Leu His Leu Val Leu Arg Leu Arg Gly Gly
290                 295                 300

Met Gln Ile Phe Val Lys Thr Leu Thr Gly Lys Thr Ile Thr Leu Glu
305                 310                 315                 320

Val Glu Ser Ser Asp Thr Ile Asp Asn Val Lys Ala Lys Ile Gln Asp
                325                 330                 335

Lys Glu Gly Ile Pro Pro Asp Gln Gln Arg Leu Ile Phe Ala Gly Lys
            340                 345                 350

Gln Leu Glu Asp Gly Arg Thr Leu Ala Asp Tyr Asn Ile Gln Lys Glu
        355                 360                 365

Ser Thr Leu His Leu Val Leu Arg Leu Arg Gly Gly Phe
370                 375                 380

<210> SEQ ID NO 3
<211> LENGTH: 1178
<212> TYPE: DNA
<213> ORGANISM: Cannabis sativa

<400> SEQUENCE: 3
gaattcaaag tcttgcagtg taattacggg ttgaaaaatt acaaaatccg catatgcagt    60
ttgatttgaa aaagtagtct aaactcacac cactcgcaca ctcatatcca aaacaaagac   120
accaaatcca aacccaaatc tagatagaaa ttgaatcata tttagatcaa aagggaacat   180
agacccgact ttagaccgca aaaccggcca agtcctaggt caacatccgg gtcacggtcc   240
tagtccgagt ctaagtttgg gtgggtgggt ccatagcttt ttttttttt ttttttgaat   300
```

| | |
|---|---|
| aaagataaac ttcattaact catgagcaat cgctcaaaag tacaacttta agttccgaag | 360 |
| ggatatcatc cttcgtgaac atacgatcag caaataatcg agactgacgt gcaaccacat | 420 |
| gtgcggctcg attagcagaa cgtttaacaa acctaatatt ccaaattttg tgtgtaagtg | 480 |
| gaagctgtgg agtgtacggc acgtcatgtt aataggtggc gtaatagaat tggaaatcct | 540 |
| aatcaatggg tttcgttttg ccctcaccat ataaataccc tcttatcctt catttctatt | 600 |
| cattactact ttctaagcga ttctcacaat aatctctgcc cccatatcaa aattcccaag | 660 |
| aacaacccta atcccttctc ttcgtacact cgttcaaggt aatcaaattc ttgcttcctt | 720 |
| agtcaaaatt gcttctgatc atagaacact cgtatatttg attttttttt tttggaatta | 780 |
| tatatatatg ttttttatat tattgaattt ctttagggtt tttaattttc gtcttatctt | 840 |
| tgaatcaacc gaataatttt tgaaaagtaa tgtactttt gttcatctgc taatttaact | 900 |
| tgtatcgtat ctttgaattt tgttagagta tttaattctc gacctgtttg tatttaattt | 960 |
| tttaaatttt accgaataat ttttggaaaa ttatacttct tttttcatct gtgaaatgta | 1020 |
| tcaataatat tgggtttcat acaattttag ggttttatta tttaatcagg caagattgtt | 1080 |
| tttttttttc ttttaaattc taagaagtt ttgtctgaaa ttatttttt ttggggata | 1140 |
| aattctgatg agattttggt ttaattgtgt aattttag | 1178 |

```
<210> SEQ ID NO 4
<211> LENGTH: 756
<212> TYPE: DNA
<213> ORGANISM: Cannabis sativa

<400> SEQUENCE: 4
```

| | |
|---|---|
| atctgtttat agctgttatg aatggaatgc attttattgt tatgtttatg gtttttatta | 60 |
| ctatgaaaca aactgctttt atgatttagt atggttaatg gtttttaaaa cttgttatat | 120 |
| atgacagttt atggtttggc cttgtggtgg tatattttca tattcagagt gagaaattct | 180 |
| ttctcatgtt tatgttcttg agttgttttt aatttgttgg ttttattaat atcaaggttt | 240 |
| taggctcaac tcgtatatga aggtctgaat ctaattattg ttgctctata gaattttcct | 300 |
| ctggccaggt tttaatggag tttaatcaca cacaccaatt acatgaaact tgattatgca | 360 |
| ttctactcta cacatatcag aattattact tcatcatcca agtatggact tatatgaaaa | 420 |
| ttgatataaa atatgaaggt tatacttcta ttgcaccagt attgtattac cttcattata | 480 |
| agtcaagaga aattttttgt gtcaattata gagttgggga gaaattgggc tttgttgcaa | 540 |
| gcaaaaaagt gaaaactaat ttagtttcta gaggaagaag aacaaatata ataaattta | 600 |
| ttttacttca acttagtta tatgtatatg tatatttatc ctagccgtct ctagttttta | 660 |
| caaggctttg gacaaaatta aaagtatta ttttacaaat acataaaaat aatatgtttt | 720 |
| tttttttttt tataaaagta cagttgttgt ggtacc | 756 |

```
<210> SEQ ID NO 5
<211> LENGTH: 51
<212> TYPE: DNA
<213> ORGANISM: Cannabis sativa

<400> SEQUENCE: 5
```

| | |
|---|---|
| cgacgttgta aaacgacggc cagtgaattc aaagtcttgc agtgtaatta c | 51 |

```
<210> SEQ ID NO 6
<211> LENGTH: 39
<212> TYPE: DNA
<213> ORGANISM: Cannabis sativa
```

```
<400> SEQUENCE: 6
gcgcgccatc atctaaaatt acacaattaa accaaaatc                              39

<210> SEQ ID NO 7
<211> LENGTH: 31
<212> TYPE: DNA
<213> ORGANISM: Cannabis sativa

<400> SEQUENCE: 7
tgtgtaattt tagatgatgg cgcgctcctc c                                      31

<210> SEQ ID NO 8
<211> LENGTH: 33
<212> TYPE: DNA
<213> ORGANISM: Cannabis sativa

<400> SEQUENCE: 8
gctataaaca gatctacagg aacaggtggt ggc                                    33

<210> SEQ ID NO 9
<211> LENGTH: 36
<212> TYPE: DNA
<213> ORGANISM: Cannabis sativa

<400> SEQUENCE: 9
ctgttcctgt agatctgttt atagctgtta tgaatg                                 36

<210> SEQ ID NO 10
<211> LENGTH: 61
<212> TYPE: DNA
<213> ORGANISM: Cannabis sativa

<400> SEQUENCE: 10
tcgactctag aggatccccg ggtaccacaa caactgtact tttataaaaa aaaaaaaaaa       60
c                                                                       61
```